United States Patent
Dyer et al.

(10) Patent No.: US 6,441,266 B1
(45) Date of Patent: Aug. 27, 2002

(54) ABSORBENT MEMBERS FOR BODY FLUIDS USING HYDROGEL-FORMING ABSORBENT POLYMER

(75) Inventors: John Collins Dyer; Stephen Allen Goldman, both of Cincinnati; Herbert Louis Retzsch, Hamilton, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/403,252

(22) PCT Filed: Apr. 9, 1998

(86) PCT No.: PCT/IB98/00537

§ 371 (c)(1), (2), (4) Date: Mar. 13, 2000

(87) PCT Pub. No.: WO98/47454

PCT Pub. Date: Oct. 29, 1998

Related U.S. Application Data

(60) Provisional application No. 60/044,628, filed on Apr. 18, 1997.

(51) Int. Cl.[7] ............................ A61F 13/15; A61F 13/20
(52) U.S. Cl. ...................... 604/368; 604/366; 604/372; 604/375; 604/378
(58) Field of Search ................................ 604/358, 366, 604/367, 368, 372, 375, 376, 378

(56) References Cited

U.S. PATENT DOCUMENTS

| | | |
|---|---|---|
| 3,669,103 A | 6/1972 | Harper et al. |
| 3,670,731 A | 6/1972 | Harmon |
| 4,529,739 A | 7/1985 | Scott et al. |
| 4,649,164 A | 3/1987 | Scott et al. |
| 4,654,039 A | 3/1987 | Brandt |
| 4,673,402 A | 6/1987 | Weisman et al. |

(List continued on next page.)

FOREIGN PATENT DOCUMENTS

| | | |
|---|---|---|
| EP | 0 532 002 A1 | 3/1993 |
| EP | 0 640 330 A1 | 3/1995 |
| EP | 0 700 672 A1 | 3/1996 |
| FR | 2732973 A1 | 10/1996 |
| WO | WO 95/17455 | 6/1995 |
| WO | WO 95/26209 | 10/1995 |
| WO | WO 96/17884 | 6/1996 |

OTHER PUBLICATIONS

Tanaka, T. et al., "Kinetics of Swelling of Gels" *J. Chem. Phys.*, vol. 70, No. 3, pp. 1214–1218 (Feb. 1, 1979).

*Primary Examiner*—John G. Weiss
*Assistant Examiner*—Michele Kidwell
(74) *Attorney, Agent, or Firm*—Carl J. Roof; Caroline Wei-Berk; Mary Catherine Hentz

(57) ABSTRACT

Absorbent members useful in the containment of body fluids such as urine, that have at least one region containing hydrogel-forming absorbent polymer in a concentration of from about 50 to 100% by weight and providing a gel-continuous fluid transportation zone when in a swollen state. This hydrogel-forming absorbent polymer has: (a) a Dynamic Gelling Rate of at least about 0.18 g/g/sec; (b) a Performance under Pressure (PUP) capacity value of at least about 25 g/g under a confining pressure of 0.7 psi (5 kPa); and (c) when the hydrogel-forming absorbent polymer is in the form of particles, a mass median particle size of at least about 100 μm.

51 Claims, 4 Drawing Sheets

U.S. PATENT DOCUMENTS

| | | |
|---|---|---|
| RE32,649 E | 4/1988 | Brandt et al. |
| 4,834,735 A | 5/1989 | Alemany et al. |
| 4,935,022 A | 6/1990 | Lash et al. |
| 4,950,692 A | 8/1990 | Lewis et al. |
| 4,970,267 A | 11/1990 | Bailey et al. |
| 5,047,023 A | 9/1991 | Berg |
| 5,102,597 A | 4/1992 | Roe et al. |
| 5,122,544 A | 6/1992 | Bailey et al. |
| 5,124,188 A | 6/1992 | Roe et al. |
| 5,147,343 A | 9/1992 | Kellenberger |
| 5,147,345 A | 9/1992 | Young et al. |
| 5,149,334 A | 9/1992 | Lahrman et al. |
| 5,149,335 A | 9/1992 | Kellenberger et al. |
| 5,154,713 A | 10/1992 | Lind |
| 5,154,714 A | 10/1992 | Nomura et al. |
| 5,217,445 A | 6/1993 | Young et al. |
| 5,248,709 A | 9/1993 | Brehm |
| 5,300,054 A | 4/1994 | Feist et al. |
| 5,350,799 A | 9/1994 | Woodrum et al. |
| 5,354,290 A | 10/1994 | Gross |
| 5,369,148 A | 11/1994 | Takahashi et al. |
| 5,384,343 A | 1/1995 | Farrar et al. |
| 5,397,845 A | 3/1995 | Rebre et al. |
| 5,399,591 A | 3/1995 | Smith et al. |
| 5,403,870 A | 4/1995 | Gross |
| 5,412,037 A | 5/1995 | Rebre et al. |
| 5,439,458 A | 8/1995 | Noel et al. |
| 5,455,284 A | 10/1995 | Dahmen et al. |
| 5,514,754 A | 5/1996 | Henderson et al. |
| 5,562,646 A | 10/1996 | Goldman et al. |
| 5,563,218 A | 10/1996 | Rebre et al. |
| 5,599,335 A | 2/1997 | Goldman et al. |
| 5,601,542 A | 2/1997 | Melius et al. |

ABSORBENT MEMBERS FOR BODY FLUIDS USING HYDROGEL-FORMING ABSORBENT POLYMER

This application is a 371 of PCT/IB98/00537 filed Apr. 9, 1998 which claims benefit of Provisional No. 60/044,628 filed Apr. 18, 1997.

TECHNICAL FIELD

This application relates to absorbent members having at least one region with a relatively high concentration of hydrogel-forming absorbent polymer having specific rates of gellation and absorbency performance under pressure.

BACKGROUND OF THE INVENTION

The development of highly absorbent members for use as disposable diapers, adult incontinence pads and briefs, and catamenial products such as sanitary napkins, is the subject of substantial commercial interest. A highly desired characteristic for such products is thinness. Thinner products are less bulky to wear, fit better under clothing, and are less noticeable. They are also more compact in the package, making the products easier for the consumer to carry and store. Smaller products allow reduced distribution costs for the manufacturer and distributor, require less shelf space required in the store per diaper unit, and require less packaging material.

The ability to provide thinner absorbent articles such as diapers is contingent on the ability to develop relatively thin absorbent cores or structures that can acquire and store large quantities of discharged body fluids such as urine or menses. In this regard, the use of certain absorbent polymers often referred to as "hydrogels," "superabsorbents" or "hydrocolloid" material has been particularly important. See, for example, U.S. Pat. No. 3,699,103 (Harper et al.), issued Jun. 13, 1972, and U.S. Pat. No. 3,770,731 (Harmon), issued Jun. 20, 1972, that disclose the use of such absorbent polymers (hereafter "hydrogel-forming absorbent polymers", or HFAPs) in absorbent articles. Indeed, the development of thinner products has been the direct consequence of thinner absorbent cores that take advantage of the ability of these hydrogel-forming absorbent polymers to absorb large quantities of discharged body fluids, typically when used in combination with a fibrous matrix as compared with a fibrous matrix alone. See, for example, U.S. Pat. No. 4,673,402 (Weisman et al.), issued Jun. 16, 1987 and U.S. Pat. No. 4,935,022 (Lash et al.), issued Jun. 19, 1990, that disclose dual-layer core structures comprising a fibrous matrix and hydrogel-forming absorbent polymers useful in fashioning thin, compact, products.

Significant prior art describes absorbent structures having relatively low amounts (e.g., less than about 50% by weight) of these hydrogel-forming absorbent polymers. See, for example, U.S. Pat. No. 4,834,735 (Alemany et al.), issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer. This fluid is not tightly held in storage cores and can be expressed by pressure or capillary contact back onto the skin of the wearer, resulting in undesirable skin wetness. In order to maintain skin dryness, such fluid must be gelled quickly and completely. Also, cores made with relatively low concentrations of HFAP are inherently relatively thick and bulky.

HFAPs are often made by polymerizing unsaturated carboxylic acids or derivatives thereof, such as acrylic acid or its salt with low levels of crosslinking monomers, typically di- or poly-functional monomer materials such as N, N'-methylenebisacrylamide, trimethylol propane triacrylate, or triallyl amine. The presence of crosslinking monomers renders these polymers water-insoluble, yet water-swellable. Higher levels of cross-linking increase gel strength while reducing gel volumes. Gel strength relates to the tendency of the hydrogel formed from these polymers to deform or "flow" under an applied stress. Gel strength needs to be such that the hydrogel formed does not deform and fill to an unacceptable degree the capillary void spaces in the absorbent structure or article, a phenomenon called "gel blocking". This would otherwise reduce the rate of absorption and the fluid distribution throughout the structure/article. Various designs have been advocated for reducing or preventing gel blocking, some of which require use of added fibrous material which tends to increase the thickness of the product undesirably. See, for example, U.S. Pat. No. 4,654,039 (Brandt et al.), issued Mar. 31, 1987 (reissued Apr. 19, 1988 as U.S. Reissue Pat. No. 32,649), U.S. Pat. No. 4,834,735 (Alemany et al.), issued May 30, 1989. U.S. Pat. No. 5,652,646 (Goldman et al.), issued Oct. 8, 1996, describes use of HFAPs which have both high porosity and high strength in high concentration cores. This patent therefore addresses the problem of gel blocking in high concentration HFAP regions by using HFAPs that retain porosity such that additional fibers are not necessary.

The effective rate at which these hydrogel-forming polymers will gel in the presence of body fluids (e.g., urine) is also important. A typical current hydrogel-forming polymer will gel completely when exposed to excess aqueous fluids such as urine over a period of about 5–20 minutes.

The rate of gellation of HFAPs in aqueous fluids has been measured by several techniques. The vortex method described in U.S. Pat. No. 5,601,542 involves addition of HFAP to a stirring aqueous solution and measuring the time required for the solution to seize and stop stirring. This patent describes absorbent cores having concentrations of HFAP of 30–100% which also have a Pressure Absorbency Index (PAI) (a value said to relate to insensitivity to pressure, infra) of at least 120 and extractables levels of less than about 13 wt. percent. Claim 29 of this patent describes similar high concentration cores made with HFAPS having a PAI of at least 120 and a vortex time of less than about 45 seconds.

The Free Swell Rate (FSR) method described in U.S. Pat. No. 5,149,335 (Kellenberger et al.) issued Sep. 22, 1992 involves determination of the time required for 1.0 g of HFAP to imbibe 20 mL of test fluid.

Yet another method involves microscopic examination of the HFAP in the gelling solution and measuring the dimensions at specific time intervals (Tanaka, T.; Fillmore, D. J. *J. Chem. Phys.*, 1979, 70, 1214).

Still another method involves spectrophotometric monitoring of a dye which is excluded from the gel in excess aqueous solution which becomes concentrated as the gel expands, as described in a Diploma Thesis by Herbert Heitmann, Universitat Dortmund Lehrstuhl fur Thermische Verfahrenstechnik, August 1989.

Each of these methods suffers from certain deficiencies. The vortex method has a subjective end point. This end point may also be unduly influenced by the presence of high molecular weight extractable components which can prematurely thicken the solution. The FSR method and the vortex method do not distinguish between fluid which is actually gelled and fluid which is loosely held interstitially, and thus can be easily expressed by pressure or capillary contact back onto the skin of the wearer. It is believed that a substantial fraction of the fluid (e.g., on the order of about 50% or more) at the FSR endpoint is held interstitially. It is further believed that the fraction of fluid held interstitially at the FSR endpoint will vary depending on particle morphology. Also, the FSR method is not usable for HFAPs which absorb the fluid very quickly as the apparent fluid uptake is achieved before all of the HFAP used in the test is wetted. The FSR method, like the vortex method, has an imprecise endpoint, which is particularly critical for very fast HFAPs. The spectrophotometric method, as described above, is not quickly responsive to changes in gel volume. Such a quick response requires minimal lag time between sampling and the reading of optical absorbency. This obviously becomes important for very fast HFAPs. Also, this method does not filter out floating pieces of small material generated during stirring which tend to interfere with the light path.

Applicants have modified the spectrophotometric method to provide data on the actual rate of gellation critical to the performance of an absorbent product. This was achieved by shortening the sampling path length to shorten the time between the actual change in optical absorbency and the spectrophotometric response to that change. Further, a self-cleaning filtration assembly was added to exclude particulate materials which can interfere with the light path. Unlike the vortex method supra, Applicants' approach is not sensitive to extractable materials which may thicken the solution (but which do not change the optical absorbency of the solution). Unlike the vortex method and the Free Swell Rate method (supra), this modified method has a specific end point independent of operator judgment. Unlike the Free Swell and Vortex methods, this method does not measure trapped interstial fluid. Unlike the Free Swell Rate method (supra), this method is also usable for very fast HFAPs useful in the present invention.

The data obtained initially show optical absorbency which is simply converted into gel volume as a function of elapsed time. The data curves showing gel volume vs. elapsed time can be fit using a simple logarithmic expression defined hereinafter. This allows unambiguous expression of the gelling curve using a single value, referred to herein as the Dynamic Gelling Rate, or DGR, in units of g/g/sec. HFAPs which exhibit faster rates without compromising other properties unacceptably have been found to be particularly preferred in specific types of absorbent core designs, described in detail hereinafter.

It has been generally recognized as desirable to have the expressed fluid converted into the gelled state as rapidly as possible. For example, U.S. Pat. No. 5,439,458 (Noel et al.) issued Aug. 8, 1995 describes absorbent articles with a "rapid acquiring, multiple layer absorbent core" using a "'high-speed" absorbent gelling material capable of reaching at least 40% of its absorbent capacity in less than or equal to about 10 seconds." U.S. Pat. No. 5,300,054 (Feist et al.) issued Apr. 5, 1994 describes absorbent cores having storage layers at least partially comprising high speed absorbent gelling material. High speed HFAPs generally have been disclosed. For example, U.S. Pat. No. 5,563,218 (Rebre et al.) issued Oct. 8, 1996 discloses a process for producing "high gel strength/short gel time acrylic polymers". U.S. Pat. No. 5,601,542 (Melius et al.) issued Feb. 11, 1997 describes absorbent composites having specified vortex times and demand gel volumes under pressure (infra). U.S. Pat. No. 5,149,335 (Kellenberger et al.) issued Sep. 22, 1992 describes use of superabsorbent material at least 15 g/g Absorbency Under Load (AUL) (infra) after 5 minutes and a Free Swell Rate of less than about 60 seconds.

U.S. Pat. No. 5,354,290 (Gross) issued Oct. 11, 1994 and U.S. Pat. No. 5,403,870 (Gross) issued Apr. 4, 1995 describe a method for producing porous HFAPs with high absorbent rates. U.S. Pat. No. 5,154,713 (Lind) issued Oct. 13, 1992, U.S. Pat. No. 4,649,164 (Scott et al.) issued Mar. 10, 1987, U.S. Pat. No. 4,529,739 (Scott et al.) issued Jul. 16, 1985, U.S. Pat. Nos. 5,154,714, and 5,399,591 describe inclusion of carbonate blowing agents in the HFAP manufacturing process to increase internal and external surface area and increase absorbent rates. World Patent 95/17,455 describes porous superabsorbents with high absorption rates generated by use of nitrogen generating initiators during the polymerization. World Patent Publication WO 96/17,884 published June, 1996, describes dispersal of solid blowing agent in the aqueous solution of monomer and crosslinker followed by heating to polymerize into a porous structure with a high rate of water absorption. The disclosure of this publication is incorporated herein by reference.

In some cases, use of high concentrations of fast HFAPs, particularly in the loading zone of the absorbent core, can actually impair fluid sorption rates. This is believed to result from rapid gellation of the HFAP with attendant tendencies to reduce porosity and/or permeability, and even gel block, and thus reduce the ability of the absorbent core to accommodate repeat insults of the body fluid. In such cases, it can be desirable to employ HFAPs with particularly high porosities and/or permeabilities so as to avoid this problem. Alternatively, a mixture of HFAP types can be employed wherein at least part of the HFAP blend has a very high rate of fluid uptake and porosity and/or permeability.

Other physical and chemical characteristics of these hydrogel-forming absorbent polymers are important to performance in absorbent structures. One characteristic is the particle size, and especially the particle size distribution, of the hydrogel-forming absorbent polymer used in the fibrous matrix. For example, particles of hydrogel-forming absorbent polymer having a particle size distribution such that the particles have a mass median particle size greater than or equal to about 400 $\mu$m have been mixed with hydrophilic fibrous materials to minimize gel blocking and to help maintain an open capillary structure within the absorbent structure so as to enhance planar transport of fluids away from the area of initial discharge to the rest of the absorbent structure. Such larger particles tend to be relatively slow to imbibe aqueous fluids. While smaller particles of HFAP will generally show faster rates of gellation, this can also lead to depressed gel volumes (when surface crosslinker, infra) and/or gel blocking as a result of such small particles. Small particles in the dry state can also be difficult to handle in manufacturing due to problems with respirable dust. Small particles in this discussion refers to generally (compact) spherical (e.g., not cylindrical as is a fiber) materials which have a maximum cross-sectional dimension of about 100 $\mu$m. Small particles, also called fines, may also be reformed into aggregates or agglomerates by additional processing (or by methods of preparation; e.g., suspension polymerization). This can minimize some of the problems associated with use of fines. However, the additional processing step can be problematic and expensive. Also, the agglomerated particles tend not to be stable during processing and usage and often release significant quantities of fines back into the absorbent product. Accordingly, it is preferred that the HFAPs useful herein not be in the form of agglomerated particles. That is, unagglomerated HFAPs are preferred herein. (FIG. 5 illustrates unagglomerated HFAP particles useful herein). Hydrogel-forming absorbent polymers useful herein can be derived from fines by impregnation with additional monomer to build up their size as described in U.S. Pat. No. 5,514,574 (Henderson et al.), issued May 7, 1996. U.S. Pat. No. 5,122,544 (Bailey et al.) issued Jun. 16, 1992 describes a process for agglomerating gel fines using difunctional epoxides. U.S. Pat. No. 4,950,692 (Lewis et al.) issued Aug. 21, 1990 and U.S. Pat. No. 4,970,267 (Bailey et al.) issued Nov. 13, 1990 similarly describe agglomeration of gel fines. U.S. Pat. No. 5,384,343 describes a process for agglomeration of fines (<50 $\mu$m into larger particles of 50–500 $\mu$m). U.S. Pat. No. 5,369,148 (Takahashi et al.) issued Nov. 29, 1994 describes a method of agglomeration of absorbent resin powder. U.S. Pat. No. 5,455,284 (Dahmen et al.) issued Oct. 3, 1995 describes recycling fines into more monomer from which a new HFAP may be formed via polymerization. U.S. Pat. No. 5,248,709 (Brehm) issued Sep. 28, 1993 describes a method for sinter granulation of fines. U.S. Pat. No. 5,350,799 (Woodrum et al.) issued Sep. 27, 1994 describes yet another process for converting fines into large particles. French Patent 2,732,973 issued October 1996, describes a process to provide a good yield of aggregated particles without fines. The above references are incorporated herein by reference.

Another important characteristic is particle size distribution of the hydrogel-forming absorbent polymer. This can be controlled to improve absorbent capacity and efficiency of the particles employed in the absorbent structure. See U.S. Pat. No. 5,047,023 (Berg), issued Sep. 10, 1991, and U.S. Pat. No. 5,397,845 (Rebre et al.) issued Mar. 14, 1995 and U.S. Pat. No. 5,412,037 (Rebre et al.) issued May 2, 1995 describing HFAPs with a narrow particle size distribution between 100 and 500 $\mu$m essentially devoid of fines. However, even adjusting the particle size distribution does not, by itself, lead to absorbent structures that can have relatively high concentrations of these hydrogel-forming absorbent polymers. See U.S. Pat. No. 5,047,023, supra (optimum fiber to particle ratio on cost/performance basis is from about 75:25 to about 90:10).

Another characteristic of these hydrogel-forming absorbent polymers that has been looked at is the level of extractables present in the polymer itself. See U.S. Pat. No. 4,654,039 (Brandt et al.), issued Mar. 31, 1987 (reissued Apr. 19, 1988 as U.S. Reissue Pat. No. 32,649). Many of these hydrogel-forming absorbent polymers contain significant levels of extractable polymer material. This extractable polymer material can be leached out from the resultant hydrogel by body fluids (e.g., urine) during the time period such body fluids remain in contact with the hydrogel-forming absorbent polymer. Such polymer material extracted by body fluid in this manner can alter the properties, e.g., increase viscosity and also electrolyte concentration of the body fluid to the extent that the fluid is more slowly absorbed and more poorly held by the hydrogel in the absorbent article.

Another important characteristic is the capillary capability of these hydrogel-forming absorbent polymers. In particular, it has been suggested that particles of these hydrogel-forming absorbent polymers be formed into interparticle crosslinked aggregate macrostructures, typically in the form of sheets or strips. See U.S. Pat. No. 5,102,597 (Roe et al.), issued Apr. 7, 1992; U.S. Pat. No. 5,124,188 (Roe et al.), issued Jun. 23, 1992; and U.S. Pat. No. 5,149,344 (Lahrman et al.), issued Sep. 22, 1992. Because the particulate nature of the absorbent polymer is retained, these macrostructures provide pores between adjacent particles that are interconnected such that the macrostructure is fluid permeable (i.e., has capillary transport channels).

Another important characteristic is gel blocking as measured in a Demand Wettability or Gravimetric Absorbence test. See, for example, U.S. Pat. No. 5,147,343 (Kellenberger), issued Sep. 15, 1992 and U.S. Pat. No. 5,149,335 (Kellenberger et al.), issued Sep. 22, 1992 where these hydrogel-forming absorbent polymers are referred to as "superabsorbent materials" and where Demand Wettability/Gravimetric Absorbence is referred to as Absorbency Under Load (AUL). "AUL" is defined in these patents as the ability of the hydrogel-forming absorbent polymer to swell against an applied restraining force (see U.S. Pat. No. 5,147,343, supra, at Col. 2, lines 43–46). The "AUL value" is defined as the amount (in mL/g or g/g) of 0.9% saline solution that is absorbed by the hydrogel-forming absorbent polymers while being subjected to a load of 21,000 dynes/cm$^2$ (about 0.3 psi). The AUL value can be reported after 1 hour (see U.S. Pat. No. 5,147,343) or 5 minutes (see U.S. Pat. No. 5,149,335). Hydrogel-forming absorbent polymers are deemed to have desirable AUL properties if they absorb at least about 24 mL/g (preferably at least about 27 mL/g) of the saline solution after 1 hour (see U.S. Pat. No. 5,147,343) or at least about 15 g/g (preferably at least about 18 g/g) of the saline solution after 5 minutes.

AUL as defined in U.S. Pat. Nos. 5,147,343 and 5,149,335 may provide some indication of which hydrogel-forming absorbent polymers will avoid gel blocking in some instances. However, AUL does not specifically determine rate of gelling or distinguish between moderately fast and very fast absorbing HFAPs. Further, AUL is inadequate for determining which hydrogel-forming absorbent polymers will provide the absorbency properties necessary for high concentration absorbent cores, as is described in U.S. Pat. No. 5,599,335 (supra). In particular, using AUL values measured according to U.S. Pat. Nos. 5,147,343 and 5,149,335 is inadequate in that they do not reflect all of the potential pressures that can be operative on the hydrogel-forming polymer in the absorbent structure. As noted above, AUL is measured in these patents at a pressure of about 0.3 psi. It is believed that a much higher confining pressure of about 0.7 psi more adequately reflects the full range of localized mechanical pressures (e.g., sitting, sleeping, squatting, taping, elastics, leg motions, other tension and torsional motions) on an absorbent structure. See U.S. Pat. No. 5,147,345 (Young et al), issued Sep. 15, 1992. Additionally, many of the absorbent structures that comprise these hydrogel-forming absorbent polymers can include other components, such as an acquisition layer that receives the initial discharge of body fluids. See, for example, U.S. Pat. No. 4,673,402 (Weisman et al), issued Jun. 16, 1987 and U.S. Pat. No. 4,935,022 (Lash et al), issued Jun. 19, 1990. This acquisition layer can comprise fibers, such as certain chemically stiffened fibers, that have a relatively high capillary suction. See, for example, U.S. Pat. No. 5,217,445 (Young et al), issued Jun. 8, 1993. To take into account these additional capillary pressures that could affect fluid acquisition by these hydrogel-forming absorbent polymers, it is more realistic to measure demand absorbency performance under a higher pressure, i.e., about 0.7 psi. This takes into better account not only the localized mechanical pressures exerted during use, but also the additional capillary pressures resulting from other components (e.g., acquisition layer) present in the absorbent structure. See U.S. Pat. No.

5,599,335 (Goldman et al.), which incorporated by reference herein, which describes a means for measuring demand absorbency under such higher pressures.

Pressure Absorbency Index (PAI) is defined in U.S. Pat. No. 5,601,542 (issued Feb. 11, 1997) Melius et al. as the sum of the AUL values determined at four pressures (0.01 psi, 0.29 psi, 0.57 psi, and 0.90 psi). This is another way of presenting AUL data as an aggregate to include the effects of pressure on AUL.

Still other characteristics for absorbent structures having relatively high concentrations of these hydrogel-forming absorbent polymers have been evaluated. See, for example, European patent application 532,002 (Byerly et al.), published Mar. 17, 1993, which identifies a characteristic called Deformation Under Load (DUL) as being important for absorbent composites having high concentrations of hydrogel-forming absorbent polymers. "DUL" is used in European patent application 532,002 to evaluate the ability of the hydrogel-forming absorbent polymer to maintain wicking channels after the absorbent polymer is swollen. See page 3, lines 9–10. Further discussion of the DUL method may be found in U.S. Pat. No. 5,562,646 (supra). U.S. Pat. No. 5,562,646 describes hydrogel-forming absorbent polymers having higher porosities that are particularly suitable for absorbent structures having high concentrations of these absorbent polymers. The openness or porosity of a hydrogel layer formed from a hydrogel-forming absorbent polymer can be defined in terms of Porosity of the Hydrogel Layer (PHL). A good example of a material having a very-high degree openness is an air-laid web of wood-pulp fibers. For example, the fractional degree of openness of an air-laid web of wood pulp fibers (e.g., having a density of 0.15 g/cc) is estimated to be 0.8–0.9, when wetted with body fluids under a confining pressure of 0.3 psi. By contrast, typical hydrogel-forming polymers such as Nalco 1180 (made by Nalco Chemical Co.) and L-761f (made by Nippon Shokubai Co., LTD) exhibit PHL values of about 0.1 or less U.S. Pat. No. 5,562,646 teaches that higher PHL values for the hydrogel-forming absorbent polymer can provide benefits in high concentration cores including (1) increased void volume in the resultant hydrogel layer for acquiring and distributing fluid; (2) increased total quantity of fluid absorbed by the absorbent polymer under demand wettability/gravimetric absorbency conditions (i.e., for the storage of fluid); (3) increased permeability of the resultant hydrogel layer for acquiring and distributing fluid; (4) improved wicking properties for the resultant hydrogel layer, such as wicking fluid upwardly against gravitational pressures or partitioning fluid away from an acquisition layer; and (5) improved swelling-rate properties for the resultant hydrogel layer to allow more-rapid storage of fluid.

U.S. Pat. No. 5,599,335 teaches the importance in cores having higher concentrations of these hydrogel-forming absorbent polymers is their permeability/flow conductivity. Permeability/flow conductivity can be defined in terms of their Saline Flow Conductivity (SFC) values. SFC measures the ability of a material to transport saline fluids, such as the ability of the hydrogel layer formed from the swollen hydrogel-forming absorbent polymer to transport body fluids. Typically, an air-laid web of pulp fibers (e.g., having a density of 0.15 g/cc) will exhibit an SFC value of about $200 \times 10^{-7}$ cm$^3$sec/g. By contrast, typical hydrogel-forming absorbent polymers such as Aqualic L-74 (made by Nippon Shokubai Co., LTD) and Nalco-1180 (made by Nalco Chemical Co.) exhibit SFC values of generally less than $1 \times 10^{-7}$ cm$^3$sec/g. Accordingly, it would be highly desirable to be able to use hydrogel-forming absorbent polymers that more closely approach an air-laid web of wood pulp fibers in terms of SFC. HFAPs having relatively high SFC values are particularly important wherein the relatively fast HFAPs of the present invention are used in the loading zone in high concentrations.

It is obvious from this discussion that no single parameter associated with HFAPs can be defined or measured to describe the suitability of a given HFAP for a given high concentration absorbent core design. Heretofore unrecognized is the importance of rate of gellation of the HFAP in concert with their ability to absorb fluid against a confining pressure.

Accordingly, it would be desirable to be able to provide an absorbent member comprising: (1) a region or regions having a relatively high concentration of hydrogel-forming absorbent polymer; (2) using HFAPs with very fast rates of gellation; (3) with relatively large particle sizes or fiber sizes; (4) that can readily acquire fluids under typical usage pressures (e.g., 0.7 psi); preferably (5) with relatively high porosities, especially when used in the loading zone, and preferably (6) permeability/flow conductivity properties more like an air-laid fibrous web.

SUMMARY OF THE INVENTION

The present invention relates to absorbent members useful in the containment of body fluids such as urine and blood. These absorbent members comprise at least one region having hydrogel-forming absorbent polymer in a concentration of from about 50 to 100% by weight. This hydrogel-forming absorbent polymer has:

(a) a Performance under Pressure (PUP) capacity value of at least about 25 g/g under a confining pressure of 0.7 psi (5 kPa);

(b) a Dynamic Gelling Rate (DGR) value of at least about 0.18 g/g/sec; and (c) when the hydrogel-forming absorbent polymer is in the form of particles, a mass median particle size of at least about 100 μm.

DETAILED DESCRIPTION OF THE INVENTION

Figure 1:
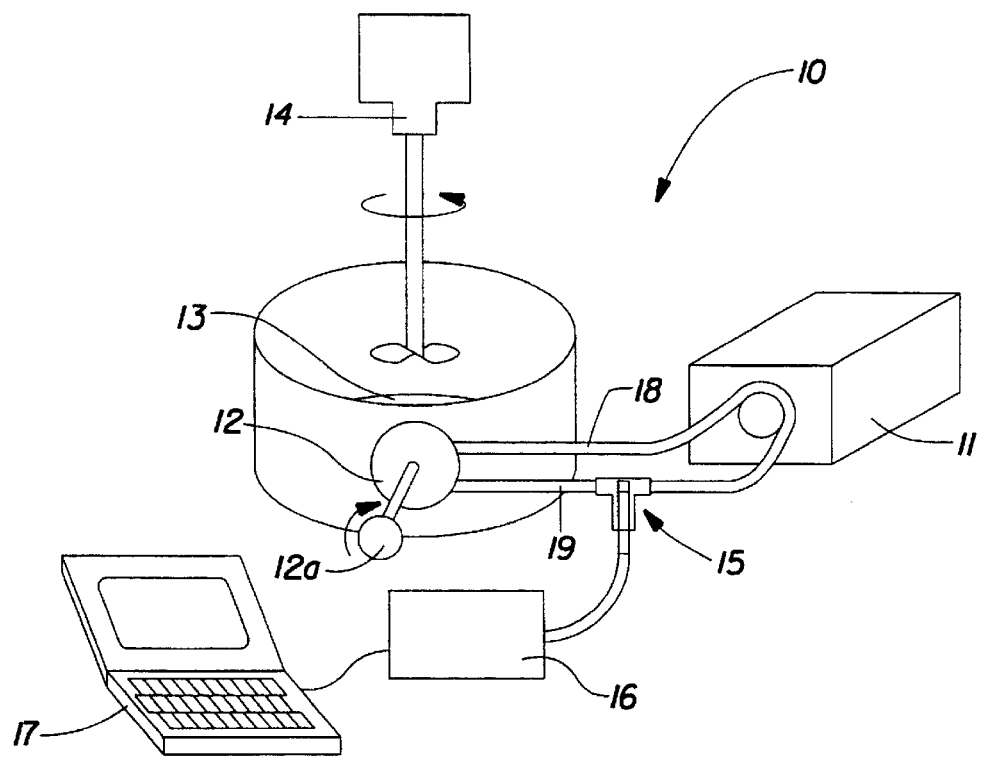
FIG. 1 is a schematic view of an apparatus for measuring the Dynamic Gelling Rate (DGR) of hydrogel-forming absorbent polymers.

The present invention relates to absorbent members useful in the containment of body fluids such as urine and blood. These absorbent members comprise at least one region having hydrogel-forming absorbent polymer in a concentration of from about 50 to 100% by weight that preferably provides a gel-continuous fluid transportation zone when in a swollen state. This hydrogel-forming absorbent polymer has:

(a) a Performance under Pressure (PUP) capacity value of at least about 25 g/g under a confining pressure of 0.7 psi (5 kPa);

(b) a Dynamic Gelling Rate (DGR) value of at least about 0.18 g/g/sec;

(c) when the hydrogel-forming absorbent polymer is in the form of particles, a mass median particle size of at least about 100 µm; and (d) preferably, a Saline Flow Conductivity (SFC) value of at least about $30 \times 10^{-7}$ cm$^3$sec/g.

A. Definitions

The following terms used herein are defined below:

"body fluids" includes urine, menses, blood, sweat, saliva, nasal mucous, and vaginal discharges.

"Z-dimension" refers to the dimension orthogonal to the length and width of the member, core or article. The Z-dimension usually corresponds to the thickness of the member, core or article.

"X-Y dimension" refers to the plane orthogonal to the thickness of the member, core or article. The X-Y dimension usually corresponds to the length and width of the member, core or article.

"absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

"absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

"region(s)" or "zone(s)" refer to portions or sections of the absorbent member.

"loading zone" means the region within the absorbent core which is impacted initially by voiding of the body fluid.

"storage zone" means an area distant from the loading zone into which the fluid is to be permanently held. "Distant" can be in either the X-Y or Z dimensions.

"porosity" means the fractional volume (dimension-less) that is not occupied by solid material and/or gel.

"layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered."

"comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

For purposes of this invention, it should also be understood that the term "upper" refers to absorbent members, such as layers, that are nearest to the wearer of the absorbent article, and typically face the topsheet of an absorbent article; conversely, the term "lower" refers to absorbent members that are furthermost away from the wearer of the absorbent article and typically face the backsheet.

All percentages, ratios and proportions used herein are by weight unless otherwise specified.

B. Material and Components of the Absorbent Member

1. Hydrogel Forming Absorbent Polymers a. Chemical Composition

The hydrogel-forming absorbent polymers useful in the present invention include a variety of water-insoluble, but water-swellable polymers capable of absorbing large quantities of fluids. Such polymers materials are also commonly referred to as "hydrocolloids, in. or "superabsorbent" materials and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, and N,N-dimethylaminoethyl or N,N-diethylaminopropyl acrylates and methacrylates, and the respective quaternary salts thereof. Typically, hydrogel-forming absorbent polymers useful in the present invention have a multiplicity of anionic, functional groups, such as metal sulfonate and carboxylate groups. Examples of polymers suitable for use herein include those which are prepared from polymerizable, unsaturated, acid-containing monomers. These monomers can be selected from olefinically unsaturated carboxylic and sulfonic acids and acid anhydrides, and mixtures thereof.

Some non-acid monomers can also be included, usually in minor amounts, in preparing the hydrogel-forming absorbent polymers herein. Such non-acid monomers can include, for example, the water-soluble or water-dispersible esters and amides of the acid-containing monomers, as well as monomers that contain no carboxylic or sulfonic acid groups at all. Optional non-acid monomers can thus include monomers containing the following types of functional groups: carboxylic acid or sulfonic acid esters and amides, hydroxyl groups, amino groups, nitrile groups, quaternary ammonium salt groups, ether groups, aryl groups (e.g., phenyl groups, such as those derived from styrene monomer). These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citraconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

Mixtures of polymers can also be used in the present invention. For example, mixtures of starch-acrylic acid graft copolymers and slightly network crosslinked polymers of partially neutralized polyacrylic acid can be used in the present invention. Mixtures or combinations of the different relatively narrow size fractions of HFAPs can be useful in the present invention, e.g., small particles in one zone and large particles in another. Mixtures or combinations of HFAPs of different morphologies may also be used, e.g., fibers in one zone and particulates in another. Small particles have a mean diameter less than about 100 $\mu$m and large particles have a mean diameter of greater than about 300 $\mu$m.

The "fast" HFAPs useful in the present invention will typically have a relatively high surface area to volume ratio. This can be achieved by varying the size, shape and/or morphology over a wide range, e.g., granules, pulverulents, interparticle aggregates, interparticle crosslinked aggregates, and the like. These can be in the form of fibers, sheets, films, foams, flakes and the like. The hydrogel-forming absorbent polymers can also comprise mixtures with low levels of one or more additives, such as for example powdered silica, surfactants, glue, binders, and the like, as referenced in U.S. Pat. No. 5,489,469. The components in this mixture can be physically and/or chemically associated in a form such that the hydrogel-forming polymer component and the non-hydrogel-forming polymer additive are not readily physically separable. The HFAPs of the present invention may also be surface treated with a polyamine such as polyethylene imine or polyallyl amine so as to confer "stickiness" when wet as described in U.S. Pat. No. 5,382,610 (Harada et al.) issued Jan. 17, 1995. This is one means for providing wet core integrity.

One preferred means of creating a relatively high surface area to volume ratio in HFAPs is to form polymers having substantial internal porosity. Porosity can be generated by several means, including inclusion of gas-generating additives (e.g., ammonium carbonate, toluene, alkanes, chlorofluorocarbons, and the like) in the polymer prior to polymerization. Examples are provided in U.S. Pat. No. 5,399,591, U.S. Pat. No. 5,154,713, U.S. Pat. No. 5,146,714, U.S. Pat. No. 5,403,870, U.S. Pat. No. 5,338,766, and U.S. Pat. No. 4,522,938, included herein by reference. A second preferred means of creating relatively high surface to volume is to form polymers in the shape of fibers, e.g., as is described in U.S. Pat. No. 5,280,079 and U.S. Pat. No. 5,026,784 included by reference herein. Indeed, fibers have a combination of properties useful herein, including speed of fluid imbibition and of relative ease of incorporation and containment in specific regions within the core structure. Yet another means is to form nonspherical shapes which are complex and have significant surface area (while not being especially porous, as described in PCT World Patents 93/19,099 and 92/16,565 (Stanley et al.) published Oct. 1, 1992. Yet another way is to select very small particles, e.g., less than about 100 $\mu$m in diameter (though this often incurs undesirable properties associated with such small sizes). Particle size is defined as the dimension determined by sieve size analysis. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et. al), issued Oct. 29, 1991, which is incorporated by reference. For HFAPs which are used in the form of fibers, the key dimensions are cross-sectional diameter and fiber length.

For particles of hydrogel-forming absorbent polymers useful in the present invention, the particles will generally have a size of at least 100 $\mu$m, and preferably will range in size from about 100 to about 2000 $\mu$m, more preferably from about 200 to about 1000 $\mu$m. The mass median particle size will be at least 100 $\mu$m, and preferably will be from about 250 to about 1000 $\mu$m, more preferably from about 300 $\mu$m to about 800 microns, and even more preferably from about 350 to about 750 $\mu$m. For HFAPs in the form of fibers, the cross-sectional diameters will generally range from about 5 $\mu$m to about 75 $\mu$m, preferably from about 10 $\mu$m to about 35 $\mu$m. The fiber lengths can be indeterminate, though generally fiber lengths must exceed cross-sectional area by at least about a factor of 10, preferably at least about a factor of 100, to be considered a fiber and not simply a distended particle. Generally, fiber lengths will be between about 2 mm and about 20 mm.

Degradation in other hydrogel-forming absorbent polymer properties such as rate (DGR), PHL, Performance Under Pressure (PUP) capacity, and level of extractable polymer. Thus, for example, it can be useful to use a size cut having a mass median size in the range of from about 350 to about 750 $\mu$m wherein only minimal mass fractions of the particulates have sizes either greater than about 750 $\mu$m or less than about 350 $\mu$m. Alternatively, a broader size cut wherein the particles generally have a size in the range of from about 250 μm to about 1000 μm can be useful.

b. Physical Properties

The following describes in detail the ranges of each of the important physical properties necessary in the present invention. It will be recognized that while the present application describes absorbent members having one or more regions of at least about 50% by weight of HFAPs where the HFAPs have certain gelling rates (DGR) and absorbency under pressure (PUP) values, it is possible to include HFAPs in the high concentration region(s) that do not exhibit these DGR and PUP capacity values, while still practicing within the scope of the present invention. That is, by way of illustration only, it is possible to include in the high concentration region(s) a mixture of one or more HFAPs wherein at least one HFAP does not exhibit a DGR value of at about least 0.18 g/g/sec and/or a PUP capacity of at least about 25 g/g, along with one or more different HFAPs that do exhibit these properties. A specific example, by way of illustration only, comprises use of a region comprising 50% by total weight HFAP wherein 20% of the HFAP (by total HFAP weight) is outside the present invention and 80% (by total HFAP weight) of the HFAP is within the present invention. In this illustration, even though only about 40% of the region(s) of the absorbent member comprises HFAPs meeting the described DGR and PUP values, the member would be within the scope of the present invention so long as the DGR and PUP values (and for particles, a mass median particle size) for a mixture within at least one region are within the scope of the present invention as described below. In this regard, it will be preferred that the high concentration region(s) of the absorbent member will comprise at least about 30% HFAPs, by total weight of the HFAPs in a region, having the DGR and PUP values described below. More preferably, the absorbent member will comprise at least about 35% HFAPs, still more preferably at least about 40% HFAPs, by total weight of the HFAPs in a region, having the DGR and PUP values described below. In such cases, the balance of HFAP used may have properties outside the present invention and will be used in an amount necessary to bring the total HFAP concentration in the region up to at least about 50%. Such mixtures of HFAPs of different types may be used homogeneously throughout the core or separately within specific regions, such as one type in the loading zone and another type in the storage zone.

(1) Rate of Gelling

A characteristic of the hydrogel-forming absorbent polymers useful in the present invention is the rate of gelling. The rate of gelling is expressed herein in terms of the Dynamic Gelling Rate (DGR) using the method described hereinafter. The HFAPs of the present invention have DGR values of at least about 0.18 g/g/sec, preferably at least about 0.25 g/g/sec, more preferably at least about 0.28 g/g/sec and most preferably at least about 0.32 g/g/sec.

(2) Performance under Pressure (PUP)

Another characteristic of the hydrogel-forming absorbent polymers useful in the present invention is their demand absorbency capacity under a high confining pressure. This demand-absorbency capacity is defined in terms of the Polymer's Performance under Pressure (PUP) capacity. The PUP capacity of hydrogel-forming absorbent polymers useful in the present invention is generally at least about 25 g/g, preferably at least about 29 g/g, and more preferably at least about 32 g/g. Typically, these PUP capacity values are in the range of from about 25 to about 45 g/g, more typically from about 29 to about 40 g/g, and most typically from about 32 to about 38 g/g. A method for determining the PUP capacity value of these hydrogel-forming absorbent polymers is provided in U.S. Pat. No. 5,599,335 (supra).

(3) Size

Still another characteristic of the hydrogel-forming absorbent polymers useful in the present invention, when in the form of particles, is their particle size. Size is defined in terms of the weight fractions that are retained or passed by sieves with different spacings, as defined hereinabove. Very small particles, less than about 100 μm, are not preferred due to their propensity to gel block, their lower gel volumes when surface crosslinked, and issues with hygiene in manufacturing environments. While larger sized particulates tend also to have slower rates of absorption, the HFAPs preferred in the present invention have a useful combination of rate and larger particle size, at least about 100 μm and preferably at least about 300 μm. Preferred ranges for mass median particle are discussed in detail, supra.

(4) Porosity of Hydrogel Zone or Layer

A characteristic that can be important for the hydrogel-forming absorbent polymers useful in the present invention is the openness or porosity of the hydrogel (PHL) zone or layer formed when the polymer is swollen in body fluids under a confining pressure. PHL measures the ability of the formed hydrogel zone or layer to remain open so as to be able to acquire and distribute body fluids under usage pressures. Porosity of the hydrogel zone or layer is also can affect the demand wettability or gravimetric absorbency capacity (i.e., PUP capacity) and wicking properties as described in U.S. Pat. No. 5,562,646 (supra). The porosity of the hydrogel zone or layer is also important because of its impact on permeability (i.e., SFC values) of the hydrogel zone/layer. Higher porosity is an important contributor to higher permeability, particularly for the very fast HFAPs of the present invention used at relatively high concentrations in the loading zone of the absorbent core.

Hydrogel-forming absorbent polymers useful in the present invention have PHL values of at least about 0.15, preferably at least about 0.18, more preferably at least about 0.18 and most preferably at least about 0.25. Typically, these PHL values are in the range of from about 0.15 to about 0.40, and more typically from about 0.18 to 0.25. A method for determining the PHL value of these hydrogel-forming absorbent polymers is provided in U.S. Pat. No. 5,562,646 (supra).

(5) Saline Flow Conductivity (SFC)

Another characteristic that can be important for the hydrogel-forming absorbent polymers useful in the present invention is their permeability or flow conductivity when swollen with body fluids so as to form a hydrogel zone or layer. This permeability or flow conductivity is defined herein in terms of the Saline Flow Conductivity (SFC) value of the hydrogel-forming absorbent polymer as described in U.S. Pat. No. 5,599,335 (supra). The SFC value of the hydrogel-forming absorbent polymers useful in the present invention is at least about $30 \times 10^{-7}$ cm$^3$sec/g, preferably at least about $50 \times 10^{-7}$ cm$^3$sec/g, and most preferably at least about $75 \times 10^{-7}$ cm$^3$sec/g. Typically, these SFC values are in the range of from about 30 to about $1000 \times 10^{-7}$ cm$^3$sec/g. A method for determining the SFC value of these hydrogel-forming absorbent polymers is provided in U.S. Pat. No. 5,599,335 (supra).

(6) Extractable Polymer

Another characteristic that can be important for hydrogel-forming absorbent polymers useful in the present invention is the level of extractable polymer material present therein. See U.S. Pat. No. 4,654,039 (Brandt et al.), issued Mar. 31, 1987 (reissued Apr. 19, 1988 as Re. 32,649). Extracted polymer material can alter both the chemical characteristics (e.g., osmolarity) and physical characteristics (e.g., viscosity) of the body fluid to such an extent that the fluid is more slowly absorbed and more poorly held by the hydrogel. Also, the PUP capacity can actually decline over time if extractables levels are too high. This is particularly problematic in the high concentration absorbent cores of the present invention.

The preferred levels of extractable polymer for hydrogel-forming absorbent polymers useful in the present invention are about 15% or less, more preferably about 10% or less, and most preferably about 7% or less of the total polymer. Methods for determining the levels of extractable polymer in these hydrogel-forming absorbent polymers invention are provided in U.S. Pat. No. 5,599,335 (supra).

(7) Gel Volume

Yet another characteristic that can be important for hydrogel-forming absorbent polymers useful in the present invention is gel volume. As used herein, the "gel volume" of a hydrogel-forming absorbent polymer is defined as its free-swell absorbent capacity when swollen in an excess of Jayco synthetic urine, unless the solution is otherwise specified. It provides a measure of the maximum absorbent capacity of the polymer under conditions of use where the pressures on the polymer are relatively low. Methods for determining the gel volumes of these hydrogel-forming polymers are provided in U.S. Pat. No. 5,599,335 (supra). The preferred gel volumes of the hydrogel-forming absorbent polymers of the present invention are at least about 25 g/g, more preferably at least about 35 g/g, and most preferably at least about 45 g/g. Typically, these gel volumes are in the range of from about 25 to about 100 g/g, more typically from about 30 to about 80 g/g, and most typically from about 35 to about 70 g/g.

(8) Gel Strength

Still another characteristic that can be important for hydrogel-forming absorbent polymers useful in the present invention is gel strength. As used herein, "gel strength" relates to the tendency of the hydrogel formed from the absorbent polymer to deform or "flow" under usage stresses. Gel strength needs to be such that the hydrogel does not deform and fill to an unacceptable degree the void spaces between the hydrogel and the other components in the absorbent member. In general, increasing gel strength will result in an increase in the permeability and porosity of a hydrogel zone or layer formed from the hydrogel-forming absorbent polymer. A method for determining the gel strength of the hydrogel-forming absorbent polymers of the present invention is provided in U.S. Pat. No. 5,599,335 (supra). It is preferred that the gel strength of the hydrogel-forming absorbent polymers of the present invention be at least about 10,000 dynes/cm$^2$, more preferably at least about 20,000 dynes/cm$^2$, and most preferably at least about 40,000 dynes/cm$^2$.

c. Methods for Making

The basic hydrogel-forming absorbent polymer can be formed in any conventional manner. Typical and preferred processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference. Other preferred methods and variations are described in more detail in U.S. Pat. No. 5,599,335 (supra).

d. Surface Crosslinking

Surface crosslinked hydrogel-forming absorbent polymers have a higher level of crosslinking in the vicinity of the surface than in the interior. As used herein, "surface" describes the outer-facing boundaries of the particle, fiber, etc. For porous hydrogel-forming absorbent polymers (e.g., porous particles, etc.), exposed internal boundaries can also be included. By a higher level of crosslinking at the surface, it is meant that the level of functional crosslinks for the hydrogel-forming absorbent polymer in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given hydrogel-forming absorbent polymer. For particulate hydrogel-forming absorbent polymers, surface crosslinking can vary with particle size, porosity, etc. Depending on variations in surface:volume ratio within the hydrogel-forming absorbent polymer (e.g., between small and large particles), it is not unusual for the overall level of crosslinking to vary within the material (e.g., be greater for smaller particles).

Surface crosslinking is generally accomplished after the final boundaries of the hydrogel-forming absorbent polymer are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced. Surface crosslinking is of particular import with the faster HFAPs of the present invention. To the extent that speed is achieved by increasing the surface area:volume ratio of the HFAP, this also exposes more surface area for surface crosslinking with potential for associated reduction in gel volume as a result. Thus, it is particularly preferable that the surface crosslinking technique be one wherein the depth of the surface is relatively thin. This is achieved more typically by use of more reactive surface crosslinking agents, described in U.S. Pat. No. 5,599,335 (supra).

Suitable general methods for carrying out surface crosslinking of hydrogel-forming absorbent polymers according to the present invention are disclosed in U.S. Pat. No. 5,597,873 (Chambers et al.) issued Jan. 28, 1997, in U.S. Pat. No. 4,541,871 (Obayashi), issued Sep. 17, 1985, U.S. Pat. No. 5,447,727 (Graham) issued Sep. 5, 1995, U.S. Pat. No. 5,385,983 (Graham) issued Jan. 31, 1995, U.S. Pat. No. 5,475,062 (Ishizaki et al.) issued Dec. 12, 1995, published PCT application WO 92/16565 (Stanley), published Oct. 1, 1992, published PCT application WO 90/08789 (Tai), published Aug. 9, 1990; published PCT application WO 93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference.

The hydrogel-forming absorbent polymer particles used in the present invention are typically substantially dry. The term "substantially dry" is used herein to mean that the particles have a fluid content, typically water or other solution content, less than about 50%, preferably less than about 20%, more preferably less than about 10%, by weight of the particles when employed to make absorbent cores or test measurements.

e. Specific Examples

The following provides some specific examples of hydrogel-forming absorbent polymers suitable for use in the present invention:

EXAMPLE 1

Properties of Hydrogel-Forming Absorbent Polymers From Commercial Sources

The properties of certain particulate partially-neutralized sodium polyacrylate hydrogel-forming polymers obtained from commercial sources useful in the present invention are shown in Table 1:

TABLE 1

| Sample Number | HFAP Type | Mfg. | Gel Volume[a] in 0.9% Saline (g/g) | DGR g/g/sec (k × GV) | PUP g/g 0.7 psi | SFC ×10$^{-7}$ cm$^3$sec/g |
|---|---|---|---|---|---|---|
| 1 | Fibersorb | Arco[1] | 57.0 | 2.13 | 6.5 | 0.1 |
| 2 | Fiberdri 1161 | Camelot[1] | 37.0 | 1.21 | 8.0 | |
| 3 | Oasis | TAL[3] | 33.7 | 0.97 | 10.2 | 10 |
| 4 | VP 101A | NSKK[4] | 29.3 | 0.55 | 15.2 | |
| 5 | M-8547 | NSKK[4] | 33.7 | 0.42 | 27.0 | 4 |
| 6 | 3936-196 | Nalco[5] | 27.0 | 0.32 | 30.7 | 32 |
| 7 | M-8161 | NSKK[4] | 36.6 | 0.30 | 33.8 | 10 |
| 8 | HC Z-5 | H-C[6] | 41.3 | 0.21 | 34.1 | 36 |
| 9 | HC Z-4 | H-C[6] | 39.9 | 0.18 | 35.3 | 20 |
| 10 | N1180 | Nalco[5] | 33.9 | 0.17 | 9.1 | 0.1 |
| 11 | L-761f | NSKK[4] | 34.0 | 0.13 | 25.4 | 5 |
| 12 | ASAP 2300 | Chemdal[2] | 38.1 | 0.099 | 35.2 | 66 |

[1]ARCO = Atlantic Richfield, Co., which sold its HFAP fiber operations to Camelot, Inc., Charlotte, NC and Calgary, Alberta.
[2]Chemdal Corporation of Palatine, Illinois.
[3]Technical Absorbents Limited, Grimsby, Great Britain.
[4]Nippon Shokubai of Hmeji, Japan.
[5]Nalco Chemical Company of Naperville, Illinois.
[6]Hoechst-Celanese of Portsmouth, VA.
[7]Stockhausen, Chemische Fabrik Stockhausen GmbH of Krefeld, Germany.
[a]Gel Volumes listed in Table 1 are measured according to the method described in the Test Methods section, except 0.9% saline is used as the test solution.

Sample numbers 5 through 9 illustrate HFAPs of the present invention. Sample numbers 1–4 have fast rates but insufficient PUP values. Samples 10–12 have rates that are slower than the HFAPs useful herein.

EXAMPLE 2

Absorbent Core of the Present Invention

An absorbent core is created by air laying a core comprising 15% fluff pulp fibers, 25% curly fibers, and 60% M8161 from Example 1. This core absorbs fluid quickly and efficiently without gel blocking.

2. Fibrous Materials

The absorbent members of the present invention can comprise fibrous materials to form fibrous web or fibrous matrices. Fibers useful in the present invention include those that are naturally occurring fibers (modified or unmodified), as well as synthetically made fibers. A detailed compendium of fibers types and their uses in absorbent cores is in U.S. Pat. No. 5,599,335 (supra).

3. Thermoplastic Materials

In the case of thermally bonded absorbent members according to the present invention, the member can comprise thermoplastic material in addition to the fibers. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers. The varied employment of thermoplastic materials in absorbent cores is detailed in U.S. Pat. Nos. 5,599,335 and 5,607,414 incorporated herein by reference.

4. Other Components and Materials

Absorbent members according to the present invention can include other optional components that can be present in absorbent webs. For example, a reinforcing scrim can be positioned within the absorbent member, or between the respective absorbent members, of the absorbent core. Such reinforcing scrims should be of such configuration as to not form interfacial barriers to fluid transfer, especially if positioned between the respective absorbent members of the absorbent core. Also, when hydrogel-forming absorbent polymers are present in one or more absorbent members of the absorbent core, the respective absorbent member, or the entire absorbent core, can be enveloped within a fluid pervious sheet, such as a tissue paper sheet, to obviate user concern regarding loose particulate absorbent polymer. Other optional components that can be included are materials to control odor, adhesives, contain fecal matter, etc.

Absorbent members according to the present invention can also include foam-based absorbents. Suitable foam absorbents include those described in U.S. Pat. No. 5,260, 345 (DesMarais et al.), issued Nov. 9, 1993, U.S. Pat. No. 5,147,345 (Young et al.), issued Sep. 15, 1992, U.S. Pat. No. 5,387,207 (Dyer et al.) issued Feb. 7, 1995, all of which are incorporated by reference.

C. Absorbent Members Containing Hydrogel-Forming Absorbent Polymers

1. Concentration, Basis Weight and Fluid Handling Properties

At least one of the absorbent members according to the present invention will comprise the previously described hydrogel-forming absorbent polymers, with or without other optional components such as fibers, thermoplastic material, etc. These absorbent members comprising these absorbent polymers can function as fluid storage members in the absorbent core. The principle function of such fluid storage members is to absorb the discharged body fluid either directly or from other absorbent members (e.g., fluid acquisition/distribution members), and then retain such fluid, even when subjected to pressures normally encountered as a result of the wearer's movements. It should be understood, however, that such polymer-containing absorbent members can serve functions other than fluid storage.

An important aspect of these absorbent members according to the present invention is that they contain one or more regions having a high concentration of these hydrogel-forming absorbent polymers. In order to provide relatively thin absorbent articles capable of absorbing and retaining large quantities of body fluids, it is desirable to increase the level of these hydrogel-forming absorbent polymers and to reduce the level of other components, in particular fibrous components.

In order to utilize these hydrogel-forming absorbent polymers at relatively high concentrations for fluid storage, these polymers should have a relatively high gelling rate (i.e., DGR value) as well as a relatively high demand absorbency capacity under a relatively high confining pressure (i.e., PUP capacity value) and preferably a relatively high permeability under pressure (i.e., SFC value) and porosity (PHL value). This is so that the polymer in the presence of body fluids acquires these discharged body fluids rapidly.

An important aspect of the present invention is that HFAPs with high rates used in the storage zone of the core also have very high SFC values. This is believed to be because very rapid gellation of the HFAP can tend to diminish the interstitial volume available which is critical for rapid imbibition of gushes. For example, baby diapers can experience gushes of 75 mL urine in 15 seconds (15 mL/second for 5 seconds). A typical diaper core might contain about 10 g of HFAP. If all 10 g were available for gelling of this gush (which is not generally the case), the rate of acquisition would have to be 15 mL urine/10 g HFAP/second, or about 1.5 g/g/sec. The high relative permeability (SFC value) substantially reduces the propensity for gel blocking in such instances.

The concentration of the hydrogel-forming absorbent polymers in a given region of an absorbent member according to the present invention can be in the range of from about 50 to 100%, preferably from about 60 to 100%, more preferably from about 70 to 100%, still more preferably from about 80 to 100%, and most preferably from about 90% to 100%, measured as defined in U.S. Pat. No. 5,599,335, which is incorporated herein by reference. The HFAPs useful in the present invention may be combined with HFAPs with properties outside those specified in the current invention. In cases wherein HFAPs of two different kinds are combined in the absorbent core, combined properties of the HFAP in the amounts and ratios specified are relevant. Another important aspect is the basis weight of the hydrogel-forming absorbent polymer in a given region of the absorbent member, which is also measured as defined in U.S. Pat. No. 5,607,414. The basis weight of a hydrogel-forming absorbent polymer in a given region of an absorbent member according to the present invention is at least about 10 gsm, preferably at least about 20 gsm, more preferably at least about 50 gsm, and most preferably at least about 100 gsm. Typically, these basis weight values are in the range of from about 10 to about 1000 gsm, more typically from about 50 to about 800 gsm, and most typically from about 100 to about 600 gsm.

2. Wet Integrity of Absorbent Member and/or Absorbent Core

During initial fluid acquisition, absorbent core utilization occurs in the immediate vicinity of the gush. There is a need to gain as much lateral (i.e., X-Y dimension) fluid movement as possible in the storage regions of the core, particularly as the absorbent cores become thinner and thinner.

The hydrogel-containing regions preferably retain a certain amount of physical continuity for adequate fluid movement to take place through contiguous interstitial voids and capillaries. Realization of the benefits of the hydrogel-forming absorbent polymers is facilitated by absorbent members and absorbent cores that provide good wet integrity. By "good wet integrity" is meant that the region or regions in the absorbent member having the high concentration of hydrogel-forming absorbent polymer have sufficient integrity in a dry, partially wet, and/or wetted state such that the physical continuity (and thus the capability of acquiring and transporting fluid through contiguous interstitial voids/capillaries) of the gel-continuous fluid transportation zone or layer formed upon swelling of the hydrogel-forming absorbent polymer in the presence of body fluids is not substantially disrupted or altered, even when subjected to normal use conditions. Such use conditions and various measures that can be taken to enhance wet integrity are described in more detail in absorbent cores is in U.S. Pat. No. 5,599,335 (supra).

D. Absorbent Cores

Absorbent members according to the present invention comprising high concentrations of hydrogel-forming absorbent polymers are useful alone or in combination with other absorbent members in a variety of absorbent cores. A wide variety of absorbent cores and their components are described in U.S. Pat. No. 5,599,335 (supra).

E. Absorbent Articles

Because of the unique absorbent properties of the absorbent cores of the present invention, they are especially suitable for use in absorbent articles, especially disposable absorbent articles. Preferred embodiments of a disposable absorbent article according to the present invention are diaper and catamenial pads. It should be understood, however, that the present invention is also applicable to other absorbent articles such as incontinent briefs, incontinent pads, training pants, diaper inserts, sanitary napkins, facial tissues, paper towels, bandages, cable wrappings, water-proofing layers, and the like.

A general description of the variety of absorbent articles which may be constructed is detailed in U.S. Pat. No. 5,599,335 (supra). These generally comprise a fluid impervious backsheet, a topsheet, an absorbent core, and various attachments (e.g., tapes, adhesives, elastics, etc.). The absorbent cores containing HFAPs of the current invention can be useful in any of the designs described therein.

F. Test Methods

1. Dynamic Gelling Rate (DGR)

This test determines the Dynamic Gelling Rate (DGR) of the hydrogel-forming absorbent polymer stirred in excess 0.03% blue dextran/0.9% sodium chloride solution (saline). This solution is prepared by dissolving 9.0 g sodium chloride and 0.300 g blue dextran (obtained from Sigma Chemical Co. Catalog Number D-5751) in 1 L distilled water. As shown in FIG. 1. the DGR testing device, depicted generally as 10, comprises a peristaltic pump 11, a self-cleaning filtering device 12 comprising a motor 12a, a hemi-spherical mixing chamber 13, an overhead stirring system 14 consisting of a motor and a stirring rod having a 2-blade propeller, a sampling assembly shown generally as 15, a colorimeter 16, and a data collecting device 17. DGR testing device 10 further comprises tubing 18 which connects filtering device 12, peristaltic pump 11 and sampling assembly 15; and tubing 19 which connects sampling assembly 15 and filtering device 12.

Figure 2A:
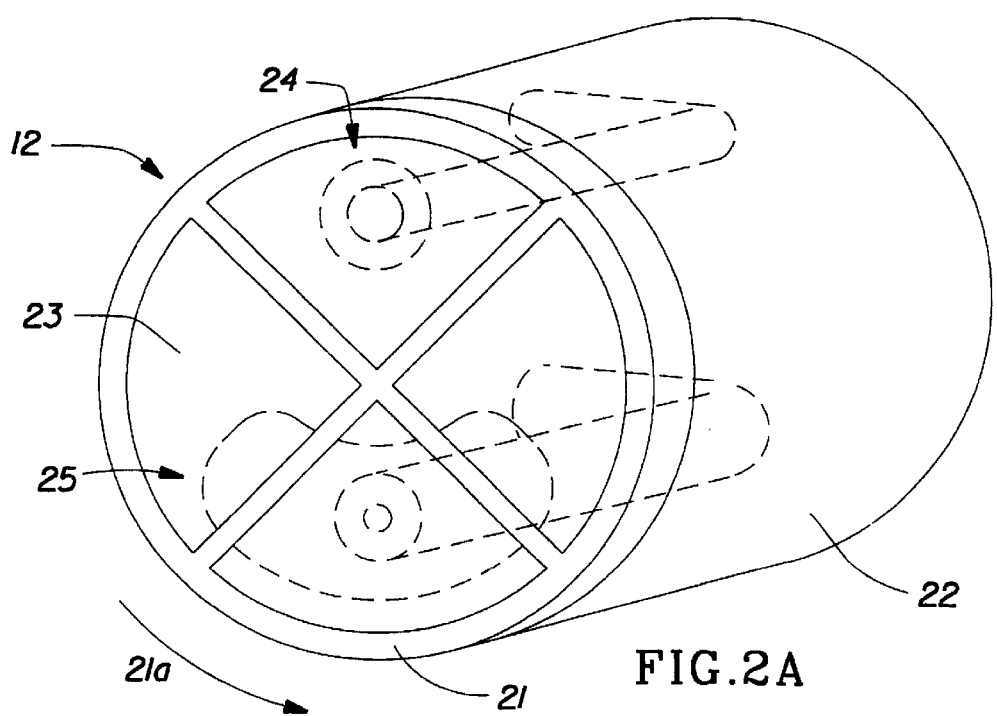
FIG. 2a is a schematic view of the self-cleaning filtering device aspect of the DGR apparatus shown in FIG. 1.
Figure 2B:
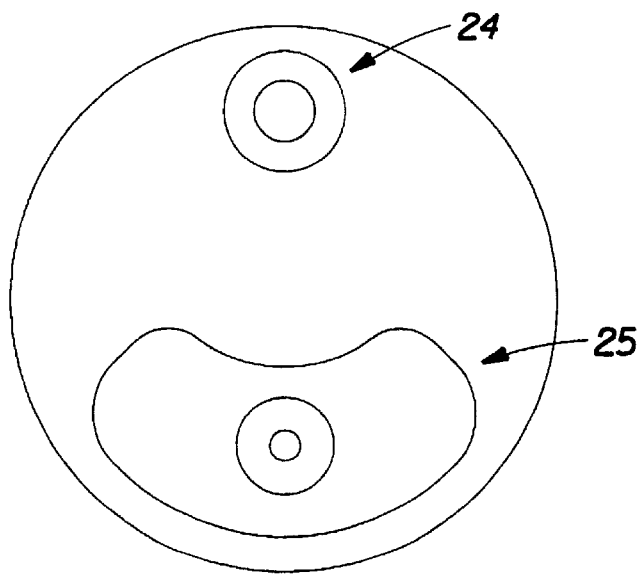
FIG. 2b is a schematic view of the filtering device depicted in FIG. 2a, but with the screen and vane removed.

The self-cleaning filtering device 12 is depicted in detail in FIG. 2a. The filtering device 12 comprises a rotating vane assembly 21, which turns in a direction 21a, a 2 in. diameter cylindrical housing 22 which is sealed into the side of the hemi-spherical mixing chamber 13, a mesh screen 23 attached to rotating vane assembly 21, an inlet port 24 and outlet port 25. Ports 24 and 25 enter cylindrical housing 22 and terminate just behind screen 23. As shown in FIG. 2b, the inlet port 24 immediately behind the screen 23 is a 0.375 in. diameter opening recessed within a 0.25 in. deep/0.5 in. diameter opening. The outlet port 25 is a 0.375 in. diameter opening within a rounded quarter moon opening which is 0.25 in. deep, 0.44 in. wide and comprises nearly the entire lower half of the cylindrical housing 22.

Figure 3:
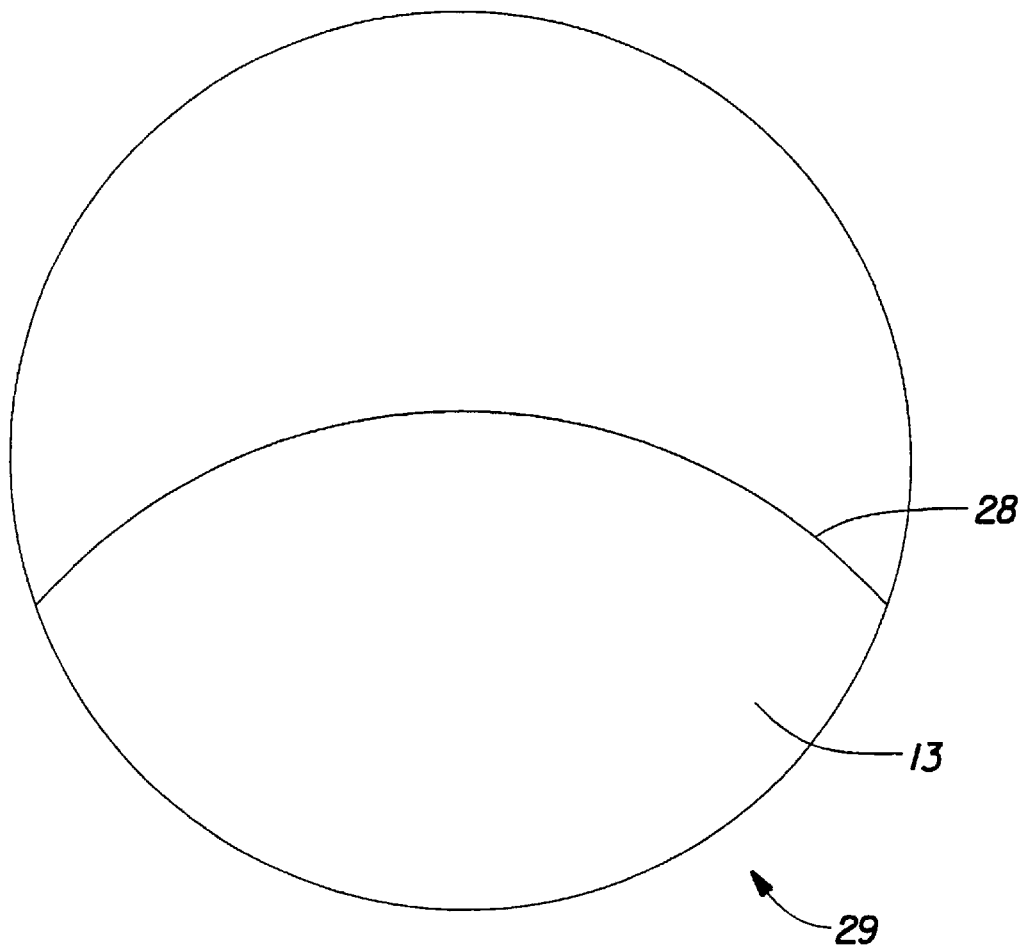
FIG. 3 is a top view of the hemispherical mixing chamber aspect of the DGR apparatus shown in FIG. 1.

The mixing chamber 13 is shown in detail in FIG. 3, and comprises machined Plexiglas® curved to form a symmetrical ( )-shaped vessel to enhance mixing. [Applicants specifically modified a cylindrical vessel (10 cm internal diameter; 7 cm deep), shown in FIG. 3 as 29, by adding a curved Plexiglas® wall 28 such that the symmetrical vessel 13 formed is 9.0 cm in the larger internal dimension, 5.3 cm in the smaller internal dimension, and 7 cm in depth. Stirring is effected with a glass paddle-style stirrer (4 cm diameter and 1.5 cm blade thickness canted at a 45° angle) from an overhead laboratory stirrer motor, the system being depicted in FIG. 1 as 14.

Figure 4A:
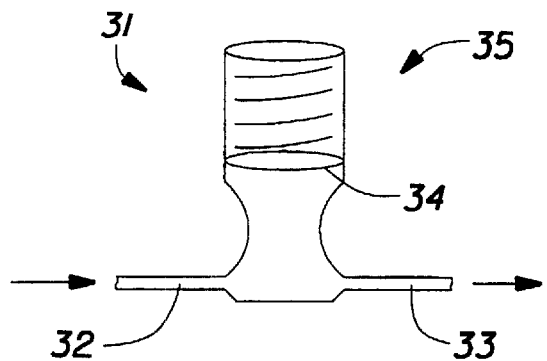
FIG. 4a is a close-up view of the sampling adapter aspect of the DGR apparatus shown in FIG. 1.
Figure 4B:
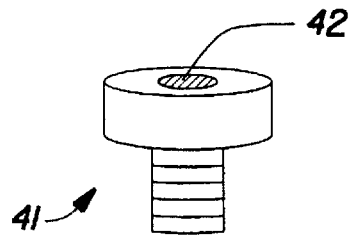
FIG. 4b is a close-up view of the probe holder aspect of the DGR apparatus shown in FIG. 1.
Figure 4C:
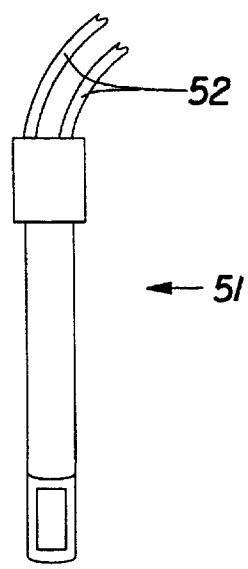
FIG. 4c is a close-up view of the fiberoptic probe aspect of the DGR apparatus shown in FIG. 1.
Figure 5:
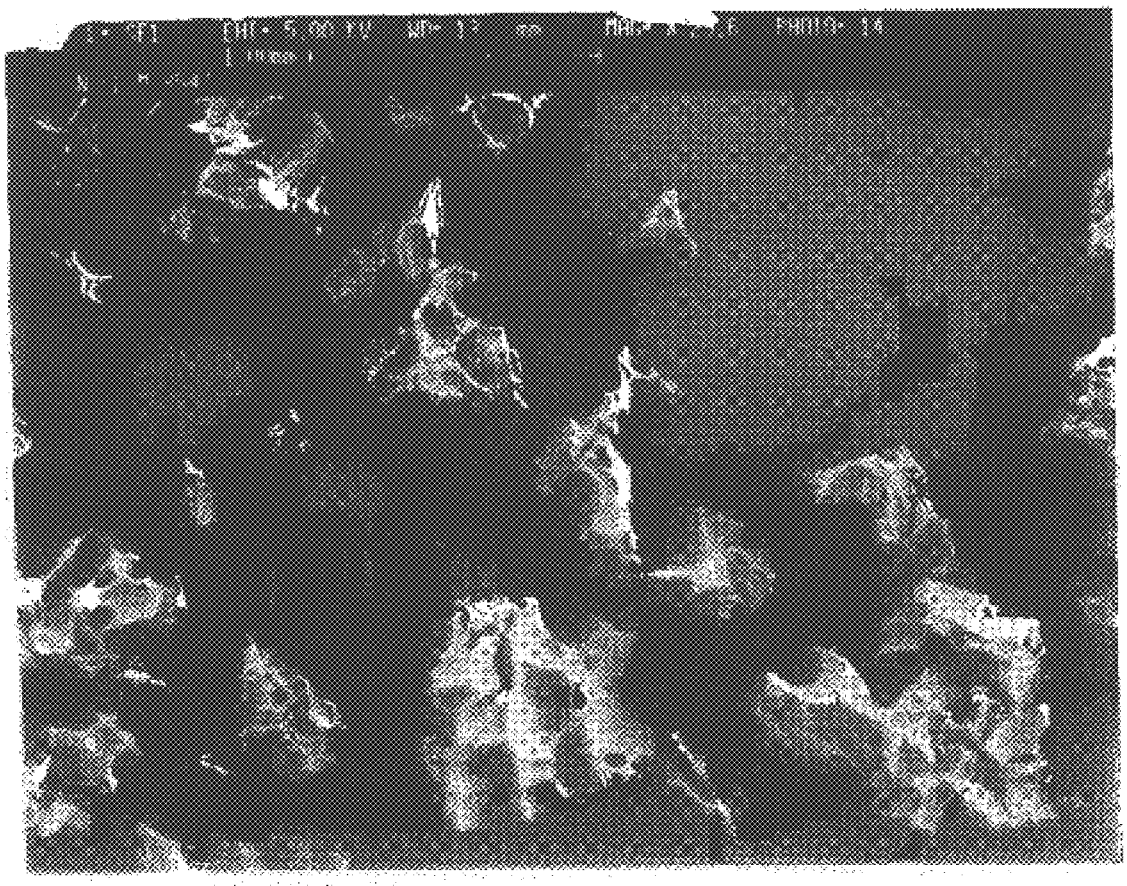
FIG. 5 is a scanning electron micrograph (SEM; 30X) of HFAP particles of the useful in the absorbent members of the present invention.

Various aspects of sample assembly 15 depicted in FIG. 1 are shown in more detail in FIGS. 4a, 4b and 4c. From these Figures, it is seen that the sample assembly comprises a threaded adapter (31 in FIG. 4a), a fiberoptic probe (51 in FIG. 4c) and a fiberoptic probe holder (41 in FIG. 4b). Adapter 31 functions to position the fiberoptic probe such that it can measure the absorbency characteristics of the fluid passing from inlet glass 32 to glass outlet 33 of adapter 31. In particular, the fiberoptic probe holder 41 shown in FIG. 4b is constructed from Teflon® and is threaded such that it can be screwed into threaded adapter 31. When probe 51 is inserted in holder 41 through hole 42 and holder 41 is tightened into adapter 31, probe 51 is securely held in place in the path of the fluid flowing through threaded adapter 31. Leads 52 of probe 51 send absorbency data to colorimeter 16. Adapter 31 is a custom made glass cell having a 2 mm i.d. glass inlet 32 and a 2 mm i.d. glass outlet 33, and also comprises a rubber O-ring 34 to ensure water-proof fit. Adapter 31 also comprises a threaded receiving body indicated generally as 35 for securely receiving probe holder 41.

With reference to all of the figures, the DGR method proceeds generally as follows. Pumping of test fluid from mixing chamber 13 to sample assembly 15 is effected via pump 11 (e.g., an easyload Masterflex model 7518-10 peristaltic pump unit) with tubing 18 (e.g., Norton Tygon® flexible tubing (⅛ in. i.d., ¼ in. o.d., 1/16 in. wall and formula R-3603 from VWR Scientific #63010-020)). Tubing 18 is replaced after 90 minutes of use or each day, whichever comes first. The sampling is through self-cleaning filtering device 12 comprising a screen 23 (e.g., a No. 400 mesh screen) attached to the rotating vane. The self-cleaning filtration device 12 is rotating at 45 rpm. To prevent the HFAP from blocking the screen, a much smaller sample return (or inlet) port 24 relative to sampling (or outlet) port 25 behind the attached screen is used to remove any gel with each revolution. The difference in pressure maintains a clean screen. The HFAP-containing solution is mixed via stirrer 14 (e.g., a T-line laboratory stirrer (model 134-2)), at a stirring rate of 640 rpm. Pump rates for peristaltic pump 11 are set to approximately 6 (approximately 250 mL/min with described tubing). This incurs a 5–7 second delay between the mixing vessel and the spectrophotometer. Although this flow can be easily increased, experience has shown that cavitation is much more likely at higher flows. Two centimeters of tubing 19 connect the outlet port 28 of the filtering device 12 to a custom made glass cell 31 (shown in FIGS. 4a–c) into which the fiber-optic probe 51 of the calorimeter fits exactly. This length of tubing is used to secure the connection and doesn't effect the distance. The actual distance from the exit port of the filtering device 12 to the probe 51 remains at 4 cm. The tubing 18 which passes from the sampling device 15 through the peristaltic pump 11 and to the sample return port 24 of the mixing chamber is 41 cm in length.

Optical absorbency readings are measured using a Brinkman Colorimeter Model PC-900 with a 620 nm bandpass filter or an equivalent colorimeter. The calorimeter 16 uses a fiberoptic probe 51 with a 2 cm (total) pathlength. Air bubbles are eliminated from the sample assembly 15 before data are collected to reduce noise.

The solution is unthermostated. The temperature during the course of these experiments should be 22°±2° C. The Colorimeter sends data every 1.26 seconds. Data are collected for at least 90 seconds via an RS-232 interface using a Toshiba 3100e computer using an appropriate interfacing software program (Symphony 2.2 with appropriate communications settings is used.) (For HFAPs outside the present invention, the rate of gelling may be so slow that 90 seconds is insufficient. At least about 30% of the full gelling curve should be taken in such cases, up to about 5 minutes.) The data are then line fit by regression analysis to provide the DGR. The following is the stepwise procedure.

Step 1. Preparing the Apparatus. To the mixing chamber 13 is added >200 mL of water. Then, the return (upper) tubing 18 is disconnected. Using a large pipette bulb, water is drawn into the tubing 18 to displace the trapped air behind the self-cleaning filtering device 12. (Displacement of nearly all trapped air is critical to this test. Very small air bubbles in the path length result in high and/or erratic absorbency readings.) Using the pipette bulb and approximately 7 mm i.d. Tygon® tubing, water is siphoned from the mixing chamber 13. The remaining water is blotted up (e.g., with Kimwipes). Two hundred grams of the 0.03% blue dextran in saline solution is weighed into a beaker and transferred to the mixing chamber 13. The volume of fluid held in tubing 18 and 19 is approximately 3.4 mL. This volume has minimal effect on the absorbency value of the blue dextran solution. If air is trapped behind the screen 23 of filtering device 12, the upper tubing 18 must be removed and the above process repeated. The components of the apparatus are activated (stirrer, peristaltic pump 11 and the self-cleaning filtering device 12) to verify that air isn't being pumped through the PC 900 probe light path.

Step 2. Begin Experiment. The computer with the appropriate software remains on at all times. The components including the colorimeter are deactivated. HFAP is weighed to approximately 1.0 gm (record weight to the nearest tenth of a milligram) onto weighing paper. Components are activated. The colorimeter is last to be activated. As the colorimeter 16 is turned on, it cycles through its start-up procedure. The data collection device 17 begins receiving data (optical absorbency (0.000)) in the light path every 1.26 seconds. The colorimeter zeroes the optical absorbency (typically 0.000 to 0.005) even though the solution contains blue dextran. The HFAP is added simultaneously to the stirring fluid in the mixing chamber 13 with the fifth reading (t=0). (Preceding null readings are deleted in the analysis.) After the desired period of data collection, the colorimeter 16 is turned off along with the self-cleaning filtering device 12/12a and the peristaltic pump 11. The final component turned off is the stirrer 14. The saline solution and the hydrated HFAP is siphoned from the mixing chamber 13 into a beaker. The chamber is replenished with approximately 200 mL of deionized water. The stirrer is reactivated and water siphoned from the chamber quickly. This is repeated a third time. A paper towel is used to dry the chamber and remove any remaining HFAP.

Step 3. Subsequent Experiments. Subsequent experiments are initiated by placing a fresh supply of blue dextran/saline solution (200.0 g) into the mixing chamber 13, removing any entrapped air from the system as described above and repeating the process beginning with all components being turned on to verify that all air has been removed. The self-cleaning filtration device 12 is rotating at 45 rpm.

Step 4: Data Analysis. Conversion from optical absorbence values to gel volume is effected using the following equation:

$$GV\ (g/g,\ t) = [1 - (A_o/(A_t + A_{o\ corr.}))] \times [\text{mL }BD\text{ soln.}/g\text{ HFAP (dry weight)}]$$

where $A_o$ is the optical absorbency reading of the stock blue dextran/saline solution. This reading is obtained separately and is typically around 0.483 for a 0.03% blue dextran (BD) solution. This can vary from lot to lot of blue dextran. $A_t$ refers to the optical absorbency reading at a given elapsed time t as recorded by the software. $A_{o\ corr.}$ is the optical absorbency reading of the stock blue dextran/saline solution corrected for the t=0 absorbency reading. As mentioned, this may vary (e.g. 0.000 to 0.005). This correction provides for the absolute change in absorbency. For example, $A_{o\ corr.}$ is 0.481 if the t=0 reading is 0.002. A corrected spreadsheet with elapsed time in one column and gel volume (g/g) in the adjacent column is prepared. A third column (Y) is generated using the equation:

$$Y = \ln\ (GV_o/(GV_o - GV_t))$$

where $GV_o$ is the final equilibrium gel volume and $GV_t$ is the gel volume at the specified elapsed time for that row. $GV_o$ may be determined from the plateau value at the end of the DGR experiment or in a separate gel volume method using blue dextran in saline as described supra. The Y data are plotted against elapsed time and the slope of the line (determined by linear regression) gives the rate constant for the reaction, k. The value k is multiplied by $GV_o$ to give the initial rate, or DGR, in units of g/g/sec. The regression coefficient, $r^2$, should be at least 0.95. Otherwise, the value for $GV_o$ should be rechecked to ensure the blue dextran has not interacted with the HFAP.

Step 5: Alternate Methods. The size-exclusion polymer used for this method should not be appreciably absorbed by the HFAP or the resultant hydrogel. For anionic HFAPs, blue dextran is particularly suitable for use as a size-exclusion polymer since it is not appreciably absorbed. For HFAPs that absorb blue dextran (e.g., cationic HFAPs), it may be necessary to use an alternative size-exclusion polymer (e.g., a high-molecular weight Dextran with a suitable covalently-bonded cationic chromophore) or an alternative detection method (e.g., refractive index, scintillation) for determining relative solution concentrations of the size-exclusion polymer. For HFAPs that appreciably absorb blue dextran, these alternative size-exclusion polymers and/or methods of detection may also need to be used for the measurement of gel volume and PHL.

What is claimed is:

1. An absorbent member for the containment of aqueous body fluids, which comprises at least one region comprising hydrogel-forming absorbent polymer in a concentration of from 50 to 100% by weight, said hydrogel-forming absorbent polymer having:
   (a) a Performance under Pressure (PUP) capacity value of at least 25 g/g under a confining pressure of 0.7 psi (5 kPa);
   (b) a Dynamic Gelling Rate (DGR) value of at least 0.18 g/g/sec; and
   (c) when the hydrogel-forming absorbent polymer is in the form of particles, a mass median particle size of at least 100 μm.

2. The absorbent member of claim 1 wherein said hydrogel-forming absorbent polymer has a DGR value of at least about 0.25 g/g/sec.

3. The absorbent member of claim 2 wherein said hydrogel-forming absorbent polymer has a DGR value of at least about 0.28 g/g/sec.

4. An absorbent core for acquiring, distributing and storing body fluids, which comprises the absorbent member of claim 3.

5. The absorbent member of claim 3 wherein said hydrogel-forming absorbent polymer has a DGR value of at least about 0.32 g/g/sec.

6. The absorbent member of claim 1 wherein said hydrogel-forming absorbent polymer has a PUP capacity value of at least about 29 g/g under a confining pressure of 0.7 psi (5 kPa).

7. An absorbent core for acquiring, distributing and storing body fluids, which comprises the absorbent member of claim 6.

8. The absorbent member of claim 6 wherein said hydrogel-forming absorbent polymer has a PUP capacity value of at least about 32 g/g under a confining pressure of 0.7 psi (5 kPa).

9. The absorbent member of claim 8 wherein said hydrogel-forming absorbent polymer is in the form of particles, and wherein the particles have a mass median particle size of from about 250 to about 1000 μm.

10. An absorbent core for acquiring, distributing and storing body fluids, which comprises the absorbent member of claim 9.

11. The absorbent member of claim 1 wherein the hydrogel-forming absorbent polymer is in the form of unagglomerated particles.

12. An absorbent core for acquiring, distributing and storing body fluids, which comprises the absorbent member of claim 11.

13. The absorbent member of claim 1 wherein said hydrogel-forming absorbent polymer has a saline flow conductivity value of at least about $30 \times 10^{-7}$ cm$^3$sec/g.

14. The absorbent member of claim 1 wherein said hydrogel-forming absorbent polymer has a Porosity of the Hydrogel Layer (PHL) of at least about 0.15.

15. The absorbent member of claim 1 wherein said hydrogel-forming absorbent polymer has less than about 15% extractable polymer material.

16. The absorbent member of claim 1 wherein said hydrogel-forming absorbent polymer has a gel volume of at least about 35 g/g.

17. The absorbent member of claim 1 wherein said hydrogel-forming absorbent polymer has a gel strength of at least about 10,000 dynes/cm$^2$.

18. The absorbent member of claim 1 wherein said hydrogel-forming absorbent polymer is in the form of particles, wherein the particles have a mass median particle size of from about 300 to about 800 μm.

19. An absorbent core for acquiring, distributing and storing body fluids, which comprises the absorbent member of claim 1.

20. An absorbent article comprising a fluid pervious topsheet, a backsheet and the absorbent core of claim 19 positioned between said topsheet and said backsheet.

21. The absorbent article of claim 26 which is a diaper.

22. The absorbent article of claim 26 which is a catamenial pad.

23. The absorbent article of claim 26 which is a wound bandage.

24. The absorbent member of claim 1 wherein at least a portion of the hydrogel-forming absorbent polymer is in the form of fibers.

25. The absorbent member of claim 24 wherein the region comprising hydrogel-forming absorbent polymer comprises at least 10% by weight fibers and at least 40% by weight particles.

26. An absorbent member for the containment of aqueous body fluids, which comprises at least one region comprising hydrogel-forming absorbent polymer in a concentration of from about 50 to 100% by weight, said hydrogel-forming absorbent polymer having:
  (a) a Performance under Pressure (PUP) capacity value of at least about 29 g/g under a confining pressure of 0.7 psi (5 kPa);
  (b) a Dynamic Gelling Rate (DGR) value of at least about 0.25 g/g/sec; and
  (c) when the hydrogel-forming absorbent polymer is in the form of particles, the mass median particle size is from about 300 to about 800 $\mu$m.

27. The absorbent member of claim 26 wherein the hydrogel-forming absorbent polymer is in the form of unagglomerated particles.

28. The absorbent member of claim 26 wherein said hydrogel-forming absorbent polymer has a saline flow conductivity value of at least about $50 \times 10^{-7}$ cm$^3$sec/g.

29. The absorbent member of claim 28 wherein said hydrogel-forming polymer has a SFC of at least about $75 \times 10^{-7}$ cm$^3$sec/g.

30. The absorbent member of claim 26 wherein said hydrogel-forming absorbent polymer has a Porosity of the Hydrogel Layer (PHL) of at least about 0.18.

31. The absorbent member of claim 30 wherein said hydrogel-forming absorbent polymer has a Porosity of the Hydrogel Layer (PHL) of at least about 0.25.

32. The absorbent member of claim 26 wherein said hydrogel-forming absorbent polymer has less than about 10% extractable polymer material.

33. The absorbent member of claim 32 wherein said hydrogel-forming absorbent polymer has less than about 7% extractable polymer material.

34. The absorbent member of claim 26 wherein said hydrogel-forming absorbent polymer has a gel volume of at least about 35 g/g.

35. The absorbent member of claim 34 wherein said hydrogel-forming absorbent polymer has a gel volume of at least about 45 g/g.

36. The absorbent member of claim 26 wherein said hydrogel-forming absorbent polymer has a gel strength of at least about 20,000 dynes/cm$^2$.

37. The absorbent member of claim 26 wherein said hydrogel-forming absorbent polymer is in the form of particles, and wherein the particles have a mass median particle size of from about 350 to about 750 $\mu$m.

38. An absorbent core for acquiring, distributing and storing body fluids, which comprises the absorbent member of claim 37.

39. The absorbent member of claim 26 wherein the basis weight of said hydrogel-forming absorbent polymer in said region is at least about 10 gsm.

40. The absorbent member of claim 26 wherein said region comprises from about 70 to 100% of said hydrogel-forming absorbent polymer.

41. The absorbent member of claim 40 wherein said region comprises from about 80 to 100% of said hydrogel-forming absorbent polymer.

42. An absorbent core for acquiring, distributing and storing body fluids, which comprises the absorbent member of claim 26.

43. An absorbent core for acquiring, distributing and storing body fluids, which comprises a fluid storage absorbent layer comprising fibrous matrix having at least one region containing particles of a surface crosslinked hydrogel-forming absorbent polymer having carboxy functional groups, said hydrogel-forming absorbent polymer being present in said region in a concentration of from about 50 to 100% by weight, said hydrogel-forming absorbent polymer providing a gel continuous fluid transportation zone when in a swollen state and having:
  (a) a Performance under Pressure (PUP) capacity value of at least about 25 g/g under a confining pressure of 0.7 psi (5 kPa);
  (b) a Dynamic Gelling Rate (DGR) value of at least about 0.18 g/g/sec;
  (c) when the hydrogel-forming absorbent polymer is in the form of particles, the mass median particle size is at least about 100 $\mu$m;
  (d) a Saline Flow Conductivity (SFC) value of from about 30 to about $1000 \times 10^{-7}$ cm$^3$sec/g;
  (e) about 15% or less extractable polymer material; and
  (f) a gel volume of from about 25 to about 100 g/g.

44. The absorbent core of claim 43 which further comprises a fluid acquisition layer.

45. The absorbent core of claim 44 wherein said fluid acquisition layer comprises chemically stiffened cellulosic fibers.

46. The absorbent core of claim 43 wherein said storage layer comprises a layer of said hydrogel-forming polymer contained between a first fibrous layer and a second fibrous layer.

47. The absorbent core of claim 46 wherein said storage layer is thermally bonded.

48. The absorbent core of claim 43 wherein said region comprises from about 70 to 100% of said hydrogel-forming polymer.

49. The absorbent core of claim 48 wherein said region comprises from about 80 to 100% of said hydrogel-forming polymer.

50. The absorbent core of claim 43 wherein the basis weight of said hydrogel-forming absorbent polymer in said region is at least about 50 gsm.

51. The absorbent core of claim 43 wherein said hydrogel-forming :absorbent polymer is selected from the group consisting of: hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers; saponified vinyl acetate-acrylic ester copolymers; hydrolyzed acrylonitrile copolymers; hydrolyzed acrylamide copolymers; slightly network crosslinked products of any of the foregoing copolymers; partially neutralized polyacrylic acid; slightly network crosslinked products of partially neutralized polyacrylic acid; and mixtures thereof.

* * * * *

UNITED STATES PATENT AND TRADEMARK OFFICE
CERTIFICATE OF CORRECTION

PATENT NO. : 6,441,266 B1
APPLICATION NO. : 09/403252
DATED : August 27, 2002
INVENTOR(S) : Dyer et al.

It is certified that error appears in the above-identified patent and that said Letters Patent is hereby corrected as shown below:

On face of patent, (57) ABSTRACT, line 8, please delete "under" and insert therefor--Under--.
    Column 4, line 57, after "generally", please delete "(compact)".
    Column 4, line 58, after "e.g.,", please insert--compact--.
    Column 7, line 52, after "importance", please insert--of permeability/flow conductivity--.
    Column 7, line 54, after "polymers", please delete "is their permeability/flow conductivity".
    Column 11, line 43, please delete "Small" and insert therefor--Generally small--.
    Column 12, line 18, please delete "PCT".
    Column 12, line 18, please delete "Patents" and insert therefor--Patent Publications--.
    Column 12, line 48, after "least", please insert--about--.
    Column 12, line 60, please delete "Degradation" and insert therefor--For some particles of some hydrogel-forming absorbent polymers, it has been found that narrower size range cuts containing generally larger particle sizes within the above specified size ranges have higher SFC values without any signification degradation--.
    Column 13, line 24, after "40%", please insert--by total weight--.
    Column 13, line 55, please delete "under" and insert therefor--Under--.
    Column 13, line 60, please delete "under" and insert therefor--Under--.
    Column 14, line 39, please delete "0.18" and insert therefor--0.20--.
    Column 17, line 16, after "certain", please delete "particulate".
    Column 17, lines 45-46, please delete "according to the method described in the Test Methods section, except 0.9% saline is used" and insert therefor--using 0.9% saline--.
    Column 17, line 47, after "solution.", please insert--These values are obtained using either the standard Gel Volume method or the DGR method.--.
    Column 19, line 9, after "high", please insert--gelling--.
    Column 19, line 20, please delete "reduces" and insert therefor--increases--.
    Column 19, lines 20-21, please delete "gel blocking" and insert therefor--rapid imbibition of gushes--.
    Column 19, line 38, please delete "5,607,414" and insert therefor--5,599,335--.
    Column 20, line 42, please delete "dissolving" and insert therefor--diluting--.
    Column 20, line 44, please delete "in" and insert therefor--to--.
    Column 20, line 44, after "1 L", please insert--with--.
    Column 20, line 45, after FIG. 1" please delete "." (the period) and insert therefor--,--(a comma).
    Column 20, line 51, please delete "testing device" and insert therefor--apparatus--.
    Column 20, line 53, please delete "peristaltic".
    Column 20, line 62, after "port 25", please insert--The self-cleaning filtration device 12 is rotating at 45 rpm.--.

UNITED STATES PATENT AND TRADEMARK OFFICE
CERTIFICATE OF CORRECTION

PATENT NO. : 6,441,266 B1
APPLICATION NO. : 09/403252
DATED : August 27, 2002
INVENTOR(S) : Dyer et al.

It is certified that error appears in the above-identified patent and that said Letters Patent is hereby corrected as shown below:

Column 21, line 21, please delete both occurrences of "glass".
    Column 21, line 24, please delete "threaded" and insert therefor--glass--.
    Column 21, line 24, after "adapter 31.", please insert--Probe 41 also comprises a built-in O-ring, which is not shown in the figures.--.
    Column 21, line 52, please delete "peristaltic".
    Column 21, line 60, please delete "calorimeter" and insert therefor--colorimeter--.
    Column 21, line 66, please delete "sample".

Column 23, lines 2-3, please delete "The self-cleaning filtration device 12 is rotating at 45 rpm.".

Column 23, line 60, please delete "under" and insert therefor--Under--.

Column 25, line 10, please delete "under" and insert therefor--Under--.

Column 26, line 15, please delete "under" and insert therefor--Under--.

Column 26, line 51, before "absorbent", please delete ":" (the colon).

Signed and Sealed this

Fifteenth Day of August, 2006

JON W. DUDAS
*Director of the United States Patent and Trademark Office*